United States Patent
Kokkin et al.

(10) Patent No.: US 9,976,955 B2
(45) Date of Patent: May 22, 2018

(54) SUB-DOPPLER INTERMODULATED LASER-INDUCED-FLUORESCENCE SPECTROMETER

(71) Applicants: Damian Kokkin, Tempe, AZ (US); Timothy Steimle, Tempe, AZ (US)

(72) Inventors: Damian Kokkin, Tempe, AZ (US); Timothy Steimle, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days. days.

(21) Appl. No.: 15/398,411

(22) Filed: Jan. 4, 2017

(65) Prior Publication Data
US 2017/0191932 A1 Jul. 6, 2017

Related U.S. Application Data

(60) Provisional application No. 62/275,530, filed on Jan. 6, 2016.

(51) Int. Cl.
*G01N 21/64* (2006.01)

(52) U.S. Cl.
CPC ....... *G01N 21/6404* (2013.01); *G01N 21/645* (2013.01); *G01N 2021/6419* (2013.01); *G01N 2021/6482* (2013.01); *G01N 2021/6491* (2013.01); *G01N 2201/0612* (2013.01)

(58) Field of Classification Search
CPC ... G01N 2021/6419; G01N 2021/6482; G01N 2021/6491; G01N 21/6404; G01N 21/645; G01N 2201/0612
See application file for complete search history.

(56) References Cited

U.S. PATENT DOCUMENTS

| | | | | |
|---|---|---|---|---|
| 3,961,188 A | * | 6/1976 | Barrett | G01T 1/1642 250/303 |
| 4,323,860 A | * | 4/1982 | Leiby, Jr. | G04F 5/14 331/3 |
| 5,390,203 A | * | 2/1995 | Miller | H01S 3/1392 372/106 |
| 5,502,562 A | * | 3/1996 | Werle | G01B 9/02004 356/486 |

(Continued)

FOREIGN PATENT DOCUMENTS

WO 2015126881 A1 8/2015

OTHER PUBLICATIONS

Ghazy, R. et al., "Sub-Doppler Laser Spectroscopy of Na2 in a Cold Molecular Beams", 2004, Egypt. J. Sol., 27(1), pp. 77-88.

(Continued)

*Primary Examiner* — Marcus Taningco
(74) *Attorney, Agent, or Firm* — Yakov S. Sidorin; Quarles & Brady LLP

(57) ABSTRACT

Optical spectroscopy system and method possessing spectral selectivity sufficient to distinguish isotopic line of the metal of interest. Each of the light beams, counter-propagating through vial with vapor of the sample, has been originated from the same light output of the laser source and modulated at a corresponding judiciously-determined frequency. The light-output, in turn, possesses a carrier frequency and two side-band frequencies defined with respect to a mean value of excitation frequencies of isotopes in the vapor.

17 Claims, 2 Drawing Sheets

(56) References Cited

U.S. PATENT DOCUMENTS

| | | | | |
|---|---|---|---|---|
| 6,790,671 | B1* | 9/2004 | Austin | B82Y 20/00 |
| | | | | 204/155 |
| 6,870,153 | B2 | 3/2005 | Goodall et al. | |
| 2009/0302957 | A1* | 12/2009 | Levi | G04F 5/145 |
| | | | | 331/94.1 |
| 2010/0246610 | A1* | 9/2010 | Mirov | C30B 31/00 |
| | | | | 372/10 |
| 2010/0267049 | A1* | 10/2010 | Rutter | G01N 21/6428 |
| | | | | 435/7.1 |
| 2012/0257661 | A1* | 10/2012 | Murphy | G01R 31/021 |
| | | | | 375/224 |
| 2014/0225678 | A1* | 8/2014 | Yano | G01R 33/26 |
| | | | | 331/94.1 |

OTHER PUBLICATIONS

Tong, W., "New laser spectroscopic technique for stable-isotope ratio analysis", Iowa State University, Retrospective Theses and Dissertations, 1984, paper 8222.

* cited by examiner

SUB-DOPPLER INTERMODULATED LASER-INDUCED-FLUORESCENCE SPECTROMETER

CROSS-REFERENCE TO RELATED APPLICATIONS

The present application claims priority from and benefit of the U.S. Provisional Patent Application No. 62/275,530 filed on Jan. 6, 2016 and titled "SUB-DOPPLER INTERMODULATED LASER-INDUCED-FLUORESCENCE SPECTROMETER." The disclosure of this provisional application is incorporated herein by reference.

TECHNICAL FIELD

The present invention relates to the field of spectrometry and, in particular, to a system and method for determination of isotopes with the use of sub-Doppler fluorescence spectroscopy and an intermodulated light source.

SUMMARY

Embodiments of the invention provide an optical system and method for implementing high-resolution optical spectroscopy employing isotopic lines of metal(s) of interest with the use of sub-Doppler measurement technique and fluorescence caused by irradiation of the isotopes with light, from a laser light source, the spectrum of which has a carrier frequency and first and second side-band frequencies and that is intermodulated.

In particular, embodiments provide an optical system for measuring fluorescence produced by isotopes. Such system includes a frequency-tunable light source configured to generate light output that has a carrier frequency and first and second side-band frequencies. The system additionally includes a system of reflectors positioned to direct first and second beams of light, formed from the light output and modulated at respectively-corresponding first and second modulation frequencies, to co-axially counter-propagate in a region of interest (ROI). The system further includes an optical detection unit configured to receive light emitted by a sample (in response to being expose to these counter-propagating beams of light) that is disposed across the first and second beams of light in the ROI.

A related embodiment of the invention provides a method containing the steps of directing first and second portions of light output, produced by a frequency-tunable light source, towards one another to define first and second co-axially counter-propagating beams; receiving fluorescence, produced by a vapor-phase sample disposed across the first and second co-axially-propagating beams, with an optical detector to form optical data; and determining a spectral characteristic of a component of the sample based on the optical data.

BRIEF DESCRIPTION OF THE DRAWINGS

The invention will be more fully understood by referring to the following Detailed Description of Specific Embodiments in conjunction with the generally not-to-scale Drawings, of which.

DETAILED DESCRIPTION

The present invention is based on the realization that the high-resolution spectroscopy can be effectuated with the use of isotopic lines of chosen materials, in one implementation—metals. Each specific metal isotope absorbs incident radiation at a slightly different, specific to such isotope wavelength(s). Accordingly, the determination of the presence and concentration and/or change in concentration of certain isotope(s) with the use of high spectral resolution laser-based spectroscopy, according to the idea of the invention, turns on the determination of the irradiance of fluorescent light, I, generated by a given isotope $$I = I_0 \exp(-\varepsilon cl) \quad (1),$$

where $I_0$ denotes incident light intensity (the intensity of excitation light from the laser source, that has been intermodulated before arriving at the isotope), c is the concentration of the given isotope in the overall isotope mixture, $\varepsilon$ is the absorption coefficient of the particular type of isotopes, and I is the path length of the excitation light through the isotope material (for example, the length of the cell containing the isotope material).

In particular, detection of a relative shift in the abundance of metal isotopes can be effectuated with the use of a spectrometer that employs counter-propagating beams of judiciously-modulated laser light. For the purposes of this disclosure, abundance refers to a relative amount of one isotope to the total amount of isotopes in a mixture of isotopes.

Figures 1A, 1B:
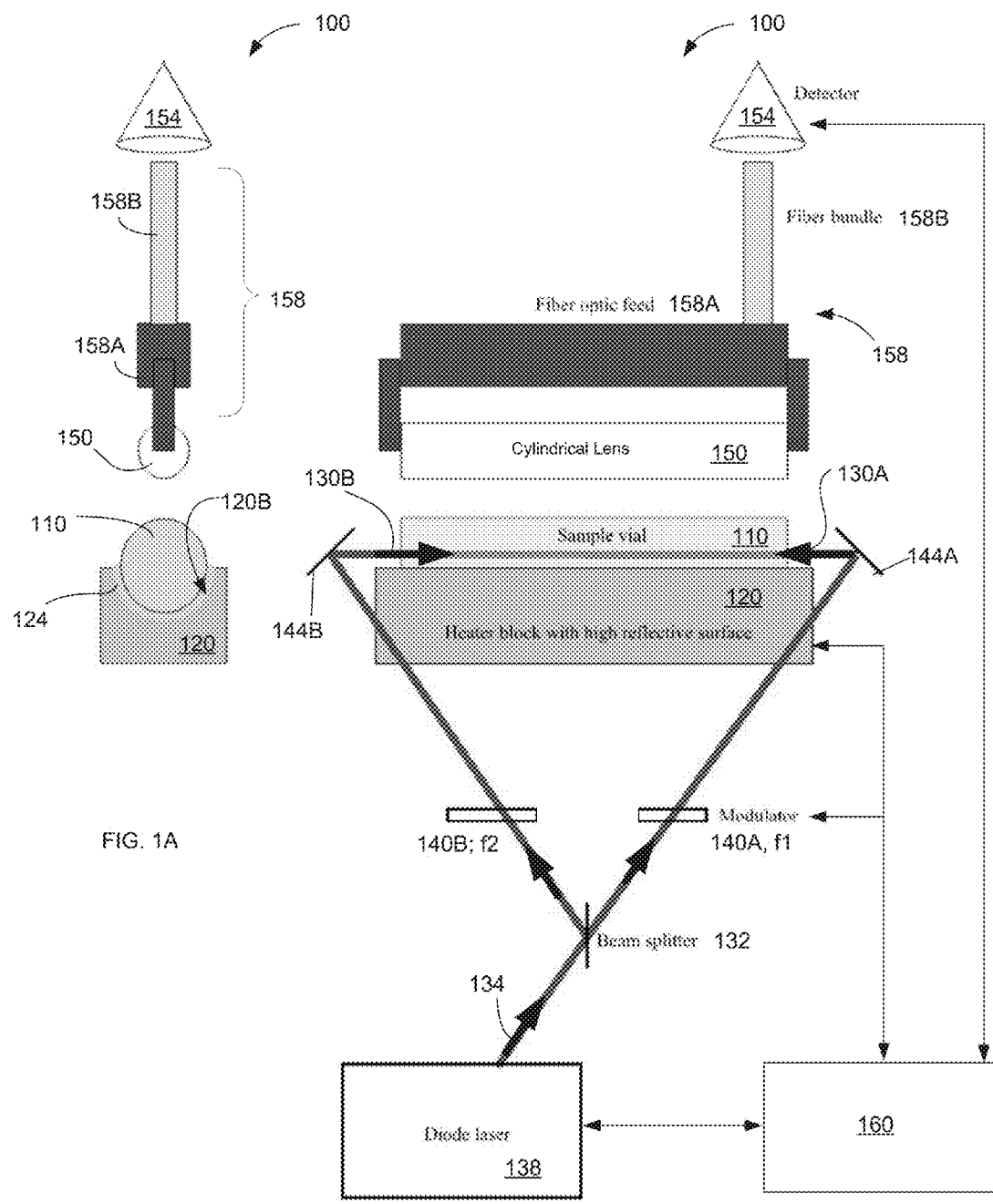
FIGS. 1A and 1B provide schematic diagrams illustrating an embodiment of the system of the invention.

FIGS. 1A, 1B schematically illustrate an embodiment 100 of the system of the invention, in side and front plan views, respectively. In this embodiment, configured to precisely measure the ratio(s) of various metal(s) isotopes, the metallic material(s) of interest is placed in a sample vial 110 (for example, made of quartz) that is heated with the heater 120 (in contact with the vial 110) to entrain a portion of the metal sample into the vapor phase inside the vial. Both the vial and the heater block are shaped such as to provide reliable physical contact between their corresponding surfaces. For example, the vial 110 has a tubular cylindrical body, while the surface 120B of the heater in contact with the vial 110 is dimensioned in a complementary fashion; as shown—to define a concave cylindrical surface with a radius substantially equal to the radius of the tubular body of the vial 110. Optionally, either an outer surface of a vial 110 or a (complementarily-shaped) surface of the heater block 120 is judiciously coated with a thin-film 124 designed to increase reflectance of light at wavelengths at which metal isotopes within the sample vial 110 fluoresce. The heater block can be heated with cartridge heaters, in one embodiment.

In the proposed scheme, a tunable-frequency laser source is used to generate resonant-frequency light for excitation of the gas-phase metal in the vial. The sub-Doppler technique of inter-modulated fluorescence is employed. The required spectral resolution is achieved by a non-linear response of the gas-phase sample to counter-propagating laser beams. The gas phase-metal is excited with light over the wavelengths of interest to detect laser-induced fluorescence (LIF) with an optical detector (and optionally—via a fiber bundle).

In particular, the vapor-phase sample in the vial 110 is irradiated with two beams of light 130A, 130B that have been formed with a beamsplitter (in one implementation—a 50/50 amplitude beam splitter 132) from the same light-output 134, produced by the laser source 138 (as shown—a laser diode). Each of the components of the original beam 134 is transmitted through a corresponding modulator (140A, 140B) so that the beams 130A, 130B contain light modulated at different rates, f1 and f2, respectively. (In one example—at 500 Hz and 1,000 Hz, respectively) to produce intermodulated beams. So-modulated (with the use of appropriately programmed electronic circuitry) light beams are then delivered, via reflectors 144A, 144B, to propagate through (traverse) the vapor-phase sample along the same axis but in different directions. In other words, intermodulated beams 130A and 130B are directed to counter-propagate (specifically, towards one another) while overlapping in space and having a common axis. Such propagation of the beams 134A, 134B is defined, for the purposes of this disclosure, with the term "co-axial counter-propagation".

The light beam 134, produced by the light source 138, has the frequency spectrum containing of which has a central, carrier frequency fC and two side-bands, fC+ and fC−. The carrier frequency fC of the beam 134 is chosen such as to be offset from mean value(s) of frequencies of emission of isotope(s) in the vial 110. Such a choice prevents the situation when two isotopes are excited by the beams 134A, 134B at once. (Otherwise, if two isotopes were excited at once, the determination of a fluorescence signal produced by a particular isotope on the background of the aggregated signal produced by these two isotopes would be substantially complicated). At the same time, the side bands of the laser-output 134, produced at the frequencies of interest fC+ and fC−, do not shift relative to the carrier frequency fC and have equal optical powers.

Due to the counter-propagating geometry of light beams 134A, 134B, chosen in this embodiment, fluorescence of interest only occurs at a frequency f_sum equal to the sum of frequencies (f1+f2). Moreover, only those atoms of metal(s) in vapor-phase material, contained in the vial 110, that have zero velocity (that is, which are stationary) interact simultaneously with the two beams 134A, 134B. Accordingly, only such stationary atoms will be caused, by light beams 134A and 134B, to fluoresce and, in contradistinction with systems of related art, the Doppler-shift does not occur during the acquisition of the required optical data.

The fluorescent light emitted by the atoms of metal isotopes is further collected with the use of a lens 150, which is dimensioned to optimize the collection of fluorescent light from the vial 110. As shown in FIGS. 1A, 1B, in one embodiment the lens 150 is configured as a cylindrical lens extended along the length of and parallel to the vial 110. The collected fluorescent radiation is further delivered to the optical detector unit 154 (which may include a photomultiplier tube, PMT, and lock-in amplifier) via an optical fiber contraption 158 (shown inclusive of the fiber optic feed 158A in operable communication with fiber cable 158B).

A skilled artisan will readily appreciate that, owing to the counter-propagation scheme of FIGS. 1A, 1B, electronic circuitry 160 (which may include a programmable processor and data-processing electronic circuitry, in operable communication with tangible, non-transitory storage medium containing program codes) may be used to govern the operation of the sub-systems of the embodiment—such as the heater module and/or light source driver, for example; to govern the operation of any of the modulators 140A, 140B, and/or to process optical data acquired from the optical detection unit 154 to extract the sought-after spectral information representing the isotope(s) of the sample in the vial 110.

In operation, the laser source 138 is scanned over the spectral frequencies representing two known atomic transitions. Relative abundances of each of the corresponding isotope is further determined from the ratio of the area of each spectral feature as given by Equation 1.

Figure 2:
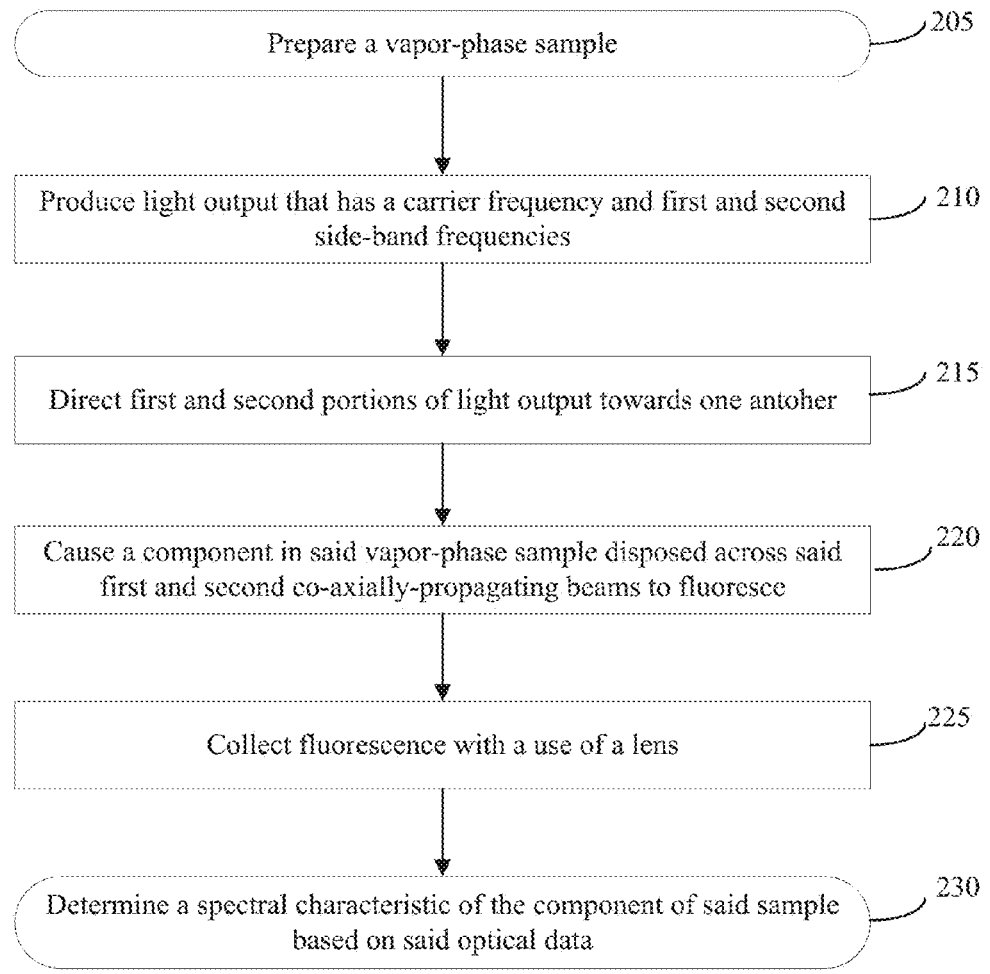
FIG. 2 illustrates an embodiment of a method for measuring fluorescence produced by isotopes.

Referring to FIG. 2, the embodiment of a method of determining a spectral characteristic of a vapor-phase sample (in one example, a vapor-phase metal isotope) is illustrated. In step 205, a portion of the metal sample is entrained into the vapor phase inside the vial 110 as described previously. In step 210, a tunable-frequency laser source is used to generate resonant-frequency light for excitation of the gas-phase metal in the vial. Further, in step 215, first and second portions of the generated excitation light (i.e., light output that has been produced by a frequency-tunable light source) are directed towards one another to define first and second co-axially counter-propagating beams. Moreover, in step 220, a component in the vapor-phase sample disposed across said first and second co-axially-propagating beams is excited to produce fluorescence. In step 225, the fluorescence, produced by the vapor-phase sample that has been disposed across the first and second co-axially-propagating beams, is collected with a use of a lens to form optical data by an optical detector. In addition, in step 230, a spectral characteristic of a component of said sample based on said optical data is determined. The sought-after spectral characteristics may include at least one of a relative abundance of the sample and spectral distribution of intensity of fluorescence produced by the sample in response to irradiation with excitation light. In generating the excitation light, care is taken to generate light output having a carrier frequency and first and second side-band frequencies, where the carrier frequency is not equal to a mean value defined by frequencies of excitation of first and second isotopes in the sample. The method further includes modulating said first and second portions at respectively-corresponding first and second frequencies that differ from one another. Optionally, the light source can be spectrally-tuned across a spectral region that includes frequencies at which first and second isotopes in the vapor-phase sample absorb light from the intermodulated first and second portions of the excitation light output.

While the invention is described through the above-described example of embodiment(s), it will be understood by those of ordinary skill in the art that modifications to, and variations of, the illustrated embodiments may be made without departing from the disclosed inventive concepts. Disclosed aspects, or portions of these aspects, may be combined in ways not listed above. Accordingly, the invention should not be viewed as being limited to the disclosed embodiment(s).

What is claimed is:

1. An optical system for measuring fluorescence produced by isotopes, the system comprising:
   a frequency-tunable light source configured to generate light output that has a carrier frequency and first and second side-band frequencies;
   an optically-transparent sample vial having a first length and a closed volume, wherein the closed volume is configured to be filled, in operation, with a sample containing a mixture of different isotopes;
   a system of reflectors positioned to direct first and second beams of light, formed from said light output and modulated at respectively-corresponding first and second modulation frequencies, to co-axially counter-propagate in a region of interest (ROI) along the first length to cause co-axially overlapped first and second beams to irradiate the sample at every point of the first length; and an optical detection unit configured to receive fluorescent light emitted only by isotopes that are stationary in said mixture, said fluorescent light emitted as a result of irradiation of the sample at said every point of the first length with the co-axially overlapped first and second beams.

2. An optical system according to claim 1, further comprising at least one optical modulator unit disposed across a corresponding one of said first and second beams of light and configured to modulate said first and second beams of light at a respectively-corresponding of said first and second modulation frequencies.

3. An optical system according to claim 1, wherein a value of the carrier frequency is defined to be offset from mean values of frequencies of emissions of any number of said two or more isotopes in the mixture.

4. An optical system according to claim 1, wherein, in operation, said vial contains the sample in a vapor-phase.

5. An optical system according to claim 1, further comprising an optical thin-film coating in optical communication with the sample vial, the optical thin-film coating configured to reflect said fluorescent light emitted by the sample in response to having been irradiated with the first and second beams of light.

6. An optical system according to claim 1, further comprising first and second optical modulators, disposed respectively across the first and second beams of light, to modulate the first beam at the first modulation frequency and the second beam at the second modulation frequency to cause said mixture to emit said fluorescent light only at a sum of the first and second modulations frequencies, wherein the first and second modulation frequencies are different from one another.

7. An optical system according to claim 1, wherein a value of the carrier frequency is defined to prevent two different isotopes in the sample to be excited at once.

8. An optical system according to claim 1, further comprising electronic circuitry cooperated with the optical detection unit to receive optical data, produced by the optical detection unit in response to acquisition of the fluorescent light, and to generate a report representing a relative abundance of isotopes in the sample.

9. An optical system according to 8, wherein said electronic circuitry is further configured to generate a report representing spectral distribution intensity of fluorescence produced by the sample.

10. A method for measuring fluorescence produced by isotopes, the method comprising:
directing first and second portions of light output, produced by a frequency-tunable light source, towards one another through an optically-transparent vial that has a first length and that is completely filled with a vapor-phase sample formed b a mixture of any number of two or more of different isotopes, to define first and second co-axially counter-propagating beams that overlap at every point of said first length;

receiving fluorescence, produced only by isotopes that are stationary in said mixture, with an optical detector to form optical data, wherein said fluorescence is emitted as a result of irradiation of the sample at said every point of the first length with the co-axially overlapped first and second beams;

and determining relative abundances of each of the different isotopes contained in said sample based on ratios of areas under curves respectively representing spectral distributions of intensity of fluorescence emitted by the different isotopes, said curves having been generated from said optical data.

11. A method according to claim 10, further comprising causing the frequency-tunable light source to generate said light output, said light output having a carrier frequency and first and second side-band frequencies, wherein the carrier frequency is not equal to a mean value defined by frequencies of excitation of first and second isotopes in said sample.

12. A method according to claim 10, further comprising modulating said first and second portions of light output at respectively-corresponding first and second frequencies, the first and second frequencies being different from one another to cause said mixture to emit said fluorescent light only at a sum of the first and second modulations frequencies.

13. A method according to claim 10, wherein said receiving and determining includes acquisition of optical data devoid of effects produced by Doppler shift to effectuate a sub-Doppler measurement of said fluorescence.

14. A method according to claim 10, further comprising spectrally-tuning said light source across a spectral region that includes frequencies at which first and second isotopes in said vapor-phase sample absorb light at said every point of the first length from the co-axially overlapped first and second beams.

15. A method according to claim 10, further comprising causing the frequency-tunable light source to generate said light output having a carrier frequency and first and second side-band frequencies, wherein the carrier frequency is defined to prevent two different isotopes in the sample to be excited at once as a result of said irradiation.

16. A method according to claim 10, further comprising heating a solid sample in said vail to form the vapor-phase sample completely filling the volume of the vail.

17. A method according to claim 10, further comprising determining a change in a relative abundance of isotopes contained in said sample.

* * * * *